United States Patent [19]

Zygraich et al.

[11] 3,962,424
[45] June 8, 1976

[54] LIVE BROVINE ADENOVIRUS VACCINES, PREPARATION THEREOF AND METHOD OF VACCINATION USING THEM

[75] Inventors: Nathan Zygraich, Brussels; Constant Huygelen, Huldenberg, both of Belgium

[73] Assignee: Recherche et Industrie Therapeutiques (R.I.T.), Belgium

[22] Filed: Aug. 13, 1975

[21] Appl. No.: 604,377

Related U.S. Application Data

[62] Division of Ser. No. 438,503, Jan. 31, 1974, Pat. No. 3,927,208.

[52] U.S. Cl. .................................................. 424/89
[51] Int. Cl.² .................. A61K 39/12; A61K 39/34
[58] Field of Search ........................................ 424/89

[56] References Cited
OTHER PUBLICATIONS

Williams et al., Chem. Abst. 76, No. 149458g (1972).
Bartha, Vet. Bull. 38, No. 147 (1968).
Mattson, Am. J. Vet. Res. 34(5): 623–629, May 1973.
Zygraich et al., Res. Vet. Sci. 16:328–335 (1974).

*Primary Examiner*—Shep K. Rose
*Attorney, Agent, or Firm*—Alan D. Lourie; William H. Edgerton

[57] ABSTRACT

The invention relates to live virus vaccines containing temperature-sensitive mutant strains of bovine Adenovirus, the cut-off temperature of said mutant strain being comprised between 39° and 40° C.

The invention also relates to the induction of said temperature-sensitive mutant strains and to a vaccination method by intranasal administration of the obtained vaccines.

8 Claims, No Drawings

LIVE BROVINE ADENOVIRUS VACCINES, PREPARATION THEREOF AND METHOD OF VACCINATION USING THEM

This application is a division of application Ser. No. 438,503, filed Jan. 31, 1974, now U.S. Pat. No. 3,927,208, which was a continuation-in-part of copending application Ser. No. 360,219, filed May 14, 1973, now abandoned.

This invention relates to the preparation of temperature-sensitive (ts) mutent strains of bovine Adenevirus strains which are valuable for the preparation of vaccines, to the live virus vaccines containing said temperature-sensitive (ts) mutant strains and to a vaccination method using said live virus vaccine.

Essentially, the substantial in vitro replication of a temperature-sensitive (ts) mutant strain is limited to temperatures inferior to its cut-off temperature. Although results obtained in vitro cannot necessarily be extrapolated to what occurs in vivo, some reports suggest that, in vivo, ts mutants behave differently from wild viruses (B. R. Murphy, E. G. Chalhud, S. R. Nusinoff and R. M. Chanock, J. of Inf. Dis. 126, no. 2, 170–8, 1972).

This phenomenon has been applied to the development of some live virus vaccines against respiratory diseases. At the best ts conditions, a ts mutant with a cut-off temperature in the range of the normal body temperature should be able to multiply in the mucosae of the upper respiratory tract (where the temperature is several degrees C lower than that of the lower respiratory tract and body) while its replication would be partially or completely inhibited in the lower respiratory tract and in the body. Studies in laboratory animals and in man have shown that, at least for some respiratory viruses, this theoretical approach is confirmed by the experimental findings (for example, N. Zygraich, M. Lobmann and C. Huygelen, J. Hyg.Camb. 70, 229–34, 1972). Nevertheless, and more particularly because of the high specificity existing in this field, it was not obvious that the same principle could be applied to other viruses, more particularly bovine Adenoviruses —e.g. Adeno 3 virus— in order to provide mutant strains valuable for the production of immunogenic and non-pathogenic live bovine Adenovirus vaccines.

This procedure circumvents the obstacles which up to now were facing the preparation of live bovine Adenovirus vaccines, i.e. the pathogenicity and side effect generating of the bovine Adenoviruses on the respiratory tract and on the gastro-intestinal tract or on the eye respectively.

We have now surprisingly found that when inducing in very specific conditions temperature-sensitive (ts) mutant strains of bovine Adenoviruses —e.g. bovine Adeno 3 virus— bovine Adenoviruses mutant strains having a cut-off temperature comprised between 39° and 40° C are isolated which are particularly suitable for vaccine use or production, owing to the fact that they are simultaneously genetically stable, immunogenic, non-pathogenic and that their administration to susceptible animals involves no detectable side effect.

A further advantage of the vaccines of this invention resides in their administration route. The vaccines of this invention indeed are administered intranasally; their constituting bovine Adenovirus strains multiply only locally in the upper respiratory tract of the animals, without any detectable virus multiplication at the warmer temperatures of the organism, i.e. in the internal organs of the animals.

For preparing the non-pathogenic bovine Adenovirus strains useful for vaccine production according to this invention, either a bovine Adenovirus —e.g. bovine Adeno 3 virus— strain directly isolated from a clinical case or a bovine Adenovirus strain obtained at the end of serial passages in tissue culture such as for instance primary bovine kidney (PBK) cell culture (such as WBR I strain —J. H. Darbyshire et al. Nature 208, 307—8, 1965—) or primary foetal bovine kidney (PFBK) cell culture may be used as starting material.

The present invention does comprise a process for preparing a non-pathogenic bovine Adenovirus —e.g. bovine Adeno 3 virus— strain from a pathogenic bovine Adenovirus strain consisting in inducing therefrom and isolating a temperature-sensitive mutant strain of bovine Adenovirus having a cut-off temperature comprised between 39° and 40° C.

According to the invention, the induction of temperature-sensitive mutant strains is performed by bringing bovine Adenovirus —e.g. Adeno 3 virus— strain into contact with a buffered aqueous solution of nitrous acid at room temperature and at a pH comprised between 4.2 and 5. The buffered aqueous solution of nitrous acid is preferably nitrous acid in acetic buffer, the concentration of nitrous acid and acetate ion in the reaction medium being N and N/4 respectively, the contact being then maintained for 2 to 5 ($\pm$ 1) minutes at pH 4.2 ($\pm$ 0.1) up to 15 to 25 minutes ($\pm$ 1) at pH 5 ($\pm$ for instance,0.1); the contact is maintained for 15 minutes ($\pm$ 1) at pH 4.6 ($\pm$ 0.1).

It is obvious that pH and temperature conditions are interrelated but the limits of the above defined conditions are such that an initial virus population of about $10^6$ is reduced to about $10^2$ after the mutagenic treatment and allow induction of temperature-sensitive mutant strains having a cut-off temperature comprised between 39° and 40° C.

The so-obtained temperature-sensitive (ts) mutant strains are then isolated by at least one passage in any tissue culture known to the art for accepting growth of said bovine Adenovirus.

For instance, isolation is possibly performed by at least one clone passage in primary foetal bovine Kidney (PFBK) cell culture, said clone passage being conducted at 30° C ($\pm$ 1° C) for a period of time comprised between 10 and 20 days, preferably for 14 days ($\pm$ 1).

The isolated strains are then optionally further passaged in any tissue culture known to the art for accepting growth of said bovine Adenovirus such as kidney cell cultures of bovine origin, and more particularly primary foetal bovine kidney cell cultures —e.g. 2 or 3 times in primary foetal bovine kidney (PFBK) cell cultures in order to get a substantial amount of said temperature-sensitive mutant strains.

An example of starting material is a pathogenic strain of bovine Adeno 3 virus obtained from the WBR 1 strain after 7 serial passages on primary foetal bovine kidney cell cultures are herein referred to as WBR 1/7 strain. A genetically stable non-pathogenic strain of bovine Adeno 3 virus obtained according to the process of the present invention has been named Eunice strain in applicant's collection where WBR 1/7 and Eunice strains samples can be obtained upon written request.

The temperature-sensitive bovine Adenovirus strains obtained by this invention —e.g. the Eunice strain— show no substantial loss of immunogenicity versus the starting pathogenic bovine Adenovirus strain; they are temperature-sensitive and non-pathogenic and valuable for live bovine Adenovirus vaccine use or production, using therefore any technique known to the art for vaccine production and stabilization. Consequently, the present invention relates to live bovine Adenovirus vaccines —e.g. Adeno 3 virus vaccine— containing at least one bovine Adenovirus strain obtained by inducing and insolating the herein described process a temperature-sensitive bovine Adenovirus mutant strain and to the process of preparing said vaccine therefrom.

According to this embodiment, the invention relates to a process for preparing a live bovine Adenovirus vaccine —e.g. an Adeno 3 virus vaccine— comprising incubating a temperature-sensitive bovine Adenovirus having a cut-off temperature comprised between 39 and 40° C in a tissue culture known to the art for accepting growth of bovine Adenovirus —e.g. primary foetal bovine (PFBK) cell culture— at a temperature not exceeding 37° C ($\pm$ 1° C) and preferably ranging 35° C ($\pm$ 1° C) and for a period of time sufficient to permit growth of a large amount of said virus, and harvesting the resulting virus material. More particularly, the said temperature-sensitive and non-pathogenic bovine Adenovirus —e.g. bovine Adeno 3 virus— is obtained as indicated above.

For the purpose of industrial and multiple batches production of the vaccine, the above production step of a large amount of said virus may obviously comprise more than one passage, the intermediate one or ones being then provide for the purpose of virus seed production to be used for preparing vaccine batches.

The so-obtained live bovine Adenovirus vaccines are administered topically in the nasopharynx at an effective dosage unit e.g. $2.10^6$ $TCID_{50}$ (tissue culture infection dose 50%) of Adeno 3 virus.

For vaccinal use, the virus is preferably kept in freeze-dried form and the vaccine is extemporaneously reconstituted by addition of either water or any other pharmaceutical diluent or composition known to the art for the preparation of nasal preparations such as coarse spray.

The invention thus also relates (1) to live bovine Adenovirus —e.g. bovine Adeno 3 virus— vaccines containing as active ingredient a temperature-sensitive bovine Adenovirus having a cut-off temperature comprised between 39° and 40° C —e.g. bovine Adeno 3 virus Eunice strain— said vaccines being more particularly obtained according to the hereabove described process, (2) to polyvalent bovine respiratory live virus vaccines administrable by intranasal route containing as active ingredients said temperature-sensitive bovine Adenovirus vaccine and at least one other bovine respiratory live virus —e.g. infectious bovine rhinotracheitis virus and/or bovine parainfluenza 3 virus— vaccine administrable by intranasal route and (3) a vaccination method consisting in administering to a susceptible organism an effective dose of said temperature-sensitive mutant strain of bovine Adenovirus.

The following examples illustrate the present invention; they should not be construed as limiting its scope.

EXAMPLE 1

Bovine Adeno 3 virus WBR 1/7 strain is suspended in tissue culture Eagle's minimal maintenance medium (MEM) to yield a virus suspension containing $10^{6.5}$ $TCID_{50}$ (tissue culture infective dose 50 %).

One ml. of this virus suspension is mixed with 0.5 ml. of a 4 M sodium nitrite aqueous solution in 0.5 ml. of molar acetic acid/sodium acetate buffer (prepared by mixing of glacial acetic acid (6 g) up to 100 ml. with distilled water and 3 volumes of a solution of sodium acetate (13.6 g.) in 100 ml. of distilled water, both solutions being sterilized for 30 minutes at 121° C), the final pH being 4.6.

The mixture is allowed to react for 15 minutes at room temperature and the reaction is then stopped by dropwise addition of normal sodium hydroxide with stirring up to reaching pH 7.5 ($\pm$ o.5). The pH adjustment is followed by changing of color of the phenol red indicator present in the virus suspension.

The medium is immediately dialyzed for 5 hours at + 4° C ($\pm$ 1) against phosphate buffer saline (consisting of NaCl (8 g.); KCl (0.2 g.); $Na_2HPO_4$ (1.15 g.); $KH_2PO_4$ (0.2 g.) in distilled water (up to 800 ml.) mixed with a solution of $MgCl_2.6H_2O$ in 100 ml. of distilled water and thereafter with a solution of $CaCl_2$ (0.1 g.) in 100 ml. of distilled water, the final solution being sterilized by filtration, the final pH being comprised between 7.2 and 7.4), this latter being renewed several times up to elimination of the nitrite anion. A sample is titrated and stored at −70° C. The titration is performed by the tube end-point dilution method in primary foetal bovine kidney tissue culture at the non-permissive temperature (39° C/$\pm$ 1° C) using 2 tubes per dilution.

After a two week incubation period, the titer is recorded and the sample stored at −70° C is diluted to contain 1 $TCID_{50}$/0.2 ml. This diluted sample is inoculated in 28 primary foetal bovine kidney tissue culture tubes using 0.1 ml. inoculum per tube. The tubes are incubated at the permissive temperature (30° C/$\pm$ 1° C). After various incubation periods ranging from 7 to 17 days, 10 inoculated tubes show a typical bovine Adeno 3 virus cytopathogenic effect; these tubes are labelled 1 to 10 and stored at −70° C. Parallel titrations of these 10 positive samples are performed at the permissive temperature (30° C) and at the non-permissive temperature (39° C). Samples exhibiting a significant difference in titer between the permissive and the non-permissive temperatures are further cloned twice by limit dilution passages.

The obtained virus is then multiplied by two passages in primary foetal bovine kidney (PFBK) cell cultures, as follows: Bovine foetuses are used as kidney donors. The kidneys are removed under aseptic conditions. Minced kidney tissue is washed in phosphate buffer saline (consisting of NaCl (8 g.); KCl (0.2 g.); $Na_2HPO_4$ (1.15 g.); $KH_2PO_4$ (0.2 g.) in distilled water (up to 800 ml.) mixed with a solution of $MgCl_2.6H_2O$ in 100 ml. of distilled water and thereafter with a solution of $CaCl_2$ (0.1 g.) in 100 ml. of distilled water, the final solution being sterilized by filtration, the final pH being comprised between 7.2 and 7.4) and trypsinized with a buffered saline solution of trypsin (2.5 g./l.) and the mixture is continuously stirred for 10 minutes at a temperature of 37° C. The liquid is then poured off and replaced by an equal volume of fresh trypsin solution. Trypsinization is then continued with stirring until exhaustion of the tissue, the cells suspended in the liquid being removed from time to time and then centrifuged at 1,000 r.p.m. and the cell sediment is suspended in growth medium (Eagle's basal medium supplemented with 10 % virus screened calf serum, 100 units of sodium penicillin G and 100 mcg. of streptomycin sulfate per ml.) to provide about 200,000 cells per ml.

One ml. samples of the cell suspension are inoculated into sterile tubes and incubated for 4 to 5 days at 37° C. At the end of this initial incubation period, the growth medium is removed and replaced in each tube by 1.5 ml. of Eagle's basal medium containing only 2 % agamma virus screened calf serum. Ten tubes are inoculated with 0.2 ml. of the hereabove obtained virus suspension and incubated at 35° C for periods varying between 7 and 14 days. The virus growth is evidenced by typical cytopathogenic effect and a passage of the virus to a second primary foetal bovine kidney (RFBK) tissue culture is carried out when about 50 % of the cells exhibit said cytopathogenic effect. The supernatant fluid is then harvested and a 0.2 ml. sample thereof is used as inoculum for the next passage.

The supernatant fluids of the second passage are harvested, pooled and diluted in a volume ratio of 1:2 with a stabilizing solution known as FC solution and consisting of casitone 60 g.; sucrose 100 g.; sodium phosphate dibasic (M/15) 75 ml.; potassium phosphate monbasic (M/15) 25 ml.; mono-potassium glutamate 20 g.; distilled water : suffcient to produce 4.25 liters and the mixture is freeze-dried to yield bovine Adeno 3 virus Eunice strain.

TS CHARACTER OF EUNICE STRAIN

Virus growth at different temperatures has been determined by titration. The results are summarized in Table I, indicating a cut-off temperature of 39.5° C (± 0.5° C). The difference in yield between Eunice strain and the parent strain WBR 1/7 is shown in Table I and demonstrates the low leakiness of Eunice strain.

TABLE I

| Strain | Virus yield $TCID_{50}$ (expressed) in $log_{10}/0.1$ ml.) | | Difference between 39.5° C and 35° C |
|---|---|---|---|
| | at 35° C | at 39.5° C | |
| WBR 1/7 | 6.5 | 6.5 | 0 |
| Eunice | 4.5 | 1.7 | 2.8 |

The stability of the ts character of Eunice strain has been demonstrated in vitro as follows:

Eunice strain has been passaged in primary foetal bovine kidney (PFBK) cell cultures at a permissive temperature (from 30° to 35° C). The results are summarized in Table II showing that the ts character remained stable throughout seven passages at 30°–35° C while the growth of the strain is considerably reduced at 39.5° C.

TABLE II

| Passage level | Virus titer $TCID_{50}$ (in $log_{10}/0.1$ ml.) | |
|---|---|---|
| | at permissive temperature (30–35° C) | at non-permissive temperature (39.5°C) |
| 1 | 5 | 0.5 |
| 4 | 6.25 | 1.5 |
| 7 | 6.3 | 1.5 |

Moreover, the ts character of the virus produced at the non-permissive temperature (39.5° C) was also tested. As indicated in Table II, Eunice strain poorly growths at the non-permissive temperature and the results of Table III indicate that the so-produced virus has kept its ts character.

TABLE III

| Titer ($log_{10}$ $TCID_{50}/0.1$ ml. at permissive and non-permissive temperatures) of virus initially produced at 39.5° C. | |
|---|---|
| Incubation temperature of virus titration | Titer |
| 35° C | 3 |
| 39.5° C | ≤ 0.5 |

EXAMPLE 2

Bovine foetal kidneys are removed under aseptic conditions, minced and washed in phosphate buffer saline (consisting of NaCl (8 g.); KCl (0.2 g.); $Na_2HPO_4$ (1.15 g.); $KH_2PO_4$ (0.2 g.) in distilled water (up to 800 ml.) mixed with a solution of $MgCl_2.6H_2O$ in 100 ml. of distilled water and thereafter with a solution of $CaCl_2$ (0.1 g.) in 100 ml. of distilled water, the final solution being sterilized by filtration, the final pH being comprised between 7.2 and 7.4) and trypsinized with a buffered saline solution of trypsin (2.5 g./l.) and the mixture is continuously stirred for 10 minutes at a temperature of 37° C. The liquid is then poured off and replaced by an equal volume of fresh trypsin solution. Trypsinization is then continued with stirring until exhaustion of the tissue, the cells suspended in the liquid being removed from time to time and then centrifuged at 1,000 r.p.m. for 5 minutes and the cell sediment is suspended in growth medium (Hank's basic salt solution supplemented with 10 % virus screened calf serum, 0.5 % lactalbumin hydrolysate, 0.1 % yeast extract and 50 mcg. of neomycin sulfate per ml.) to provide about 200,000 cells per ml.

Aliquots (one ml.) of the cell suspension are inoculated into 500 square centimeter culture flasks and incubated for 4 to 5 days at 37° C. At the end of this initial incubation period, the growth medium is removed and the cell monolayer is washed twice with a maintenance medium consisting of Earle's basic salt solution containing 0.5 % lactalbumin hydrolysate; 0.1 % yeast extract; 0.1 % tryptose phosphate broth and 50 mcg. of neomycin sulfate per ml.

Each bovine foetal kidney cell culture flask is inoculated with one ml. of a suspension of bovine Adeno 3 virus Eunice strain in distilled water and containing about $2.10^6$ $TCID_{50}$ml. (i.e. at the multiplicity index of 0.1). Maintenance medium (same composition as the above washings) is added to each flask and the culture is incubated at a temperature of 35° C for a period of time sufficient to permit growth of a large amount of virus, i.e. for at least 5 to 10 days as evidenced by typical cytopathogenic effect of bovine Adeno 3 virus.

The supernatant fluids are then harvested, pooled and diluted in a volume ratio of 1:2 with a stabilizing solution known as FG solution and consisting of casitone 60 g.; sucrose 100 g.; sodium phosphate dibasic (M/15) 75 ml.; potassium phosphate monobasic (M/15) 25 ml.; monopotassium glutamate 20 g.; distilled water sufficient to produce one liter.

The preparation is distributed into glass vials containing either $2.10^6$ $TCID_{50}$ or multiples thereof and the vials are freeze-dried and sealed for constituting either single or multiple doses. After reconstitution by adding four ml. of water per dosis, the vaccine is administered as coarse spray to the animal.

a. Vaccination program.

The so-obtained vaccine was inoculated by intranasal way to 9 animals (6 months old calves) at a dosage unit of $2.10^6$ TCID$_{50}$ (two ml. per nostril). The animals were selected for their variable serological state reproducing conditions existing within the bovine population in Europe (for instance, CH. Ludwig and H. Liebermann : Monatsch. Vat. Med. 25, 229, 1970 and G. Wellemans et J. Leunen:Vlaams Diergen. Tijdschr. 3, 125, 1968).

b. Virus re-isolation after vaccination.

Samples obtained by nasal swabbing were checked for presence of virus in the nasal cavities.

The virus re-isolated from the nose of the vaccinated animals has been passaged in culture tubes of secondary foetal bovine tissue incubated for 14 days at 35°C, all the negative samples being subpassaged in the same conditions and culture system.

The final results are indicated in Table IV.

TABLE IV

| Reference number of the animal | Animal status | Day of re-isolation after vaccination | | | | | | |
|---|---|---|---|---|---|---|---|---|
| | | 3 | 4 | 5 | 6 | 7 | 10 | 11 |
| 70 | indirect control | – | – | – | – | – | – | – |
| 72 | indirect control | – | – | – | – | – | – | – |
| 71 | direct control | – | – | – | – | – | – | – |
| 73 | direct control | – | – | – | – | – | – | – |
| 74 | vaccinated | – | – | + | – | – | – | – |
| 75 | vaccinated | – | – | – | – | – | – | – |
| 76 | vaccinated | + | + | – | + | – | – | – |
| 77 | vaccinated | (+) | – | – | – | – | – | – |
| 78 | vaccinated | – | + | – | + | – | – | – |
| 79 | vaccinated | – | + | – | – | – | – | – |
| 80 | vaccinated | (+) | – | – | – | – | – | – |
| 81 | vaccinated | + | (+) | – | – | – | – | – |
| 82 | vaccinated | + | + | (+) | + | – | – | – |

(+) = positive in subpassage.

These results indicate that the vaccine virus was re-isolated from all the vaccinated animals, veal 75 excepted. R-isolation was obtained from 3 to 6 days postvaccination. Among the 15 re-isolations, 4 were obtained by subpassages. As resulting from the virological examination conducted during the 11 day period following vaccination, the direct controls were not contaminated by the vaccinated animals. Tentatives of re-isolation from the feces were all negative and demonstrate innocuity of the vaccine of the invention due to the restricted multiplication of the vaccine virus strain; i.e. in the upper respiratory tract.

c. Ts character of the vaccine virus re-isolated after vaccination.

Titration and determination of the ts character were performed in secondary foetal bovine kidney tissue cultures, said cultures being washed before inoculation in order to eliminate residual bovine serum. For each dilution, 4 or 5 tubes were inoculated with 0.1 ml. The cultures were incubated at 35° C and the titers were determined by estimation of the cytopathogenic effect, after a 14 day incubation period.

As indicated in Table V, testing of the ts character of the virus re-isolated from the nose of the vaccinated animals demonstrates stability of the ts character of the vaccine virus Eunice strain after in vivo passage.

TABLE V

| Virus origin | Day of re-isolation after vaccination | Virus titer TCID$_{50}$ (expressed in log$_{10}$/ 0.1 ml.) at the temperature of : | | | | |
|---|---|---|---|---|---|---|
| | | 35°C | 38°C | 38.5°C | 39°C | 39.5°C |
| Animal 74 | 5 | 3.75 | 3.75 | 3.25 | 2.25 | ≤ 0.5 |
| Animal 76 | 6 | 4.75 | 4.75 | 3.5 | 2.75 | ≤ 0.5 |
| Animal 78 | 6 | 3.5 | 3.25 | 3.25 | 2.5 | ≤ 0.5 |
| Animal 82 | 6 | 4.75 | 4.25 | 4.25 | 3.25 | ≤ 0.5 |
| WBR 1/7 | – | 4.25 | 4.75 | 5 | 5 | 5.25 |
| Eunice | – | 5.25 | 5.50 | ND | ND | 1.5 |

ND = not determined.

d. Virus re-isolation after challenge.

All the animals were challenged 27 days after vaccination with WBR 1/7 strain, using $10^7$ TCID$_{50}$ per nostril.

The virus re-isolated from the nose of the vaccinated animals has been passaged in curture tubes of secondary foetal bovine kidney tissue incubated for 14 days at 39.5° C, all the negative samples being subpassaged in the same conditions and culture system.

The final results are indicated in Table VI.

TABLE VI

| Reference number of the animal | Animal status | Day of re-isolation after challenge | | | | |
|---|---|---|---|---|---|---|
| | | 3 | 4 | 6 | 7 | 10 |
| 70 | indirect control | + | + | + | – | – |
| 72 | indirect control | + | + | – | – | + |
| 71 | direct control | + | – | – | – | – |
| 73 | direct control | + | – | – | – | + |
| 74 | vaccinated | – | – | – | – | – |
| 75 | vaccinated | – | – | – | – | – |
| 76 | vaccinated | – | – | – | – | – |
| 77 | vaccinated | –(+) | – | – | – | – |
| 78 | vaccinated | – | – | – | – | – |
| 79 | vaccinated | – | – | – | – | – |
| 80 | vaccinated | – | – | – | – | – |
| 81 | vaccinated | – | – | – | – | – |
| 82 | vaccinated | + | – | – | – | – |

(+) = positive in subpassage.

The results of Table VI indicate that the challenge virus was only isolated from two among the nine vaccinated animals and only on the third day after challenge. In contrast, virus was recovered from the nose of all control animals. Particularly, indirect controls (70 and 72) had 3 positive samples on a total of 5, during the 10 day post challenge observation period.

Table VI demonstrates that there is no multiplication of the challenge virus in the nasal cavities of the vaccinated animals.

c. Seroconversion after vaccination.

The serological testing was performed by seroneutralization using the constant virus (100 TCID$_{50}$)/serum dilution technique, the first dilution being 1/4.

The sera were previously inactivated by heating at 56° C for 30 minutes and each serum dilution was brought into contact with the virus for 1 hour at 35° C before being distributed into culture tubes (0.2 ml. per tube) using four tubes for each serum dilution. The inoculated tubes were incubated at 35° C and serum titers were determined after a 14 day incubation period.

The results of the seroneutralization test are given in Table VII.

TABLE VII

| Reference number of the animal | Animal status | Day of sampling versus vaccination day | | | |
|---|---|---|---|---|---|
| | | −1 | 13 | 27(challenge) | 42(15 days after chall.) |
| 70 | indirect control | 4 | <8 | G2A4 | 16 |
| 72 | indirect control | 64 | 64 | 64 | 256 |
| 71 | direct control | 128 | 128 | ⩾ 256 | 512 |
| 73 | direct control | ⩾ 128 | 128 | 128 | 1024 |
| 74 | vaccinated | 32 | ⩾ 256 | 512 | 512 |
| 75 | vaccinated | 128 | ⩾ 256 | ⩾ 1024 | ⩾ 2048 |
| 76 | vaccinated | 32 | ⩾ 256 | 512 | 1024 |
| 77 | vaccinated | ⩾ 128 | ⩾ 256 | 256 | 256 |
| 78 | vaccinated | 32 | ⩾ 256 | 256 | 256 |
| 79 | vaccinated | 32 | ⩾ 256 | ⩾ 1024 | 2048 |
| 80 | vaccinated | 16 | ⩾ 256 | 512 | 512 |
| 81 | vaccinated | ⩾ 128 | ⩾ 256 | 256 | 2048 |
| 82 | vaccinated | 8 | 128 | 128 | 128 |

These results show that animals having an antibody titer of 128 or less at the time of vaccination already reacted 13 days after vaccination. In contrast, the direct or indirect controls (except animal 71) does not show any significant increase of titer during the same observation period.

The results after challenge indicate a significative increase of antibodies titer among all the control animals (animal 71 excepted) while no significative increase was observed among all the vaccinated animals (animal 81 excepted).

The results demonstrate the high antigenicity of the vaccine according to the invention.

f. Serological characteristics of nasal secretions.

The testing of the neutralizing potency of nasal secretions was carried out by neutralization of the nasal secretions using the constant nasal sample dose/virus dilution technique.

The nasal secretion sampling was carried out by washing of the nasal cavities with 50 ml. of normal saline per nostril. The washings were then sonicated and concentrated by ultrafiltration to 1/10 of their initial volume.

The neutralizing potency of the nasal secretions is given in Table VIII wherein they are expressed by their neutralization index for 0.1 ml. of the concentrated sample.

TABLE VIII

| Reference number of the animal | Animal status | Neutralization index (days versus vaccination) | | | |
|---|---|---|---|---|---|
| | | −1 | 11 | 17 | 27 |
| 70 | indirect control | 1 | 0 | 1 | 1 |
| 72 | indirect control | 0 | 0 | ND | ND |
| 71 | direct control | 3 | 0 | 0 | 0 |
| 73 | direct control | 0 | 0 | 0 | 0 |
| 74 | vaccinated | 0 | 3 | 3 | 3 |
| 75 | vaccinated | 1 | >4 | >4 | >4 |
| 76 | vaccinated | 0 | 2 | ND | 2 |
| 77 | vaccinated | 0 | 3 | 3 | 0 |
| 78 | vaccinated | 0 | 1 | 1 | 2 |
| 79 | vaccinated | 0 | 3 | 3 | 1 |
| 80 | vaccinated | 0 | 3 | 1 | 2 |
| 81 | vaccinated | 0 | 3 | ND | 3 |
| 82 | vaccinated | 0 | 1 | 1 | 0 |

ND = not determined.

Table VIII indicates that 11 days after vaccination with a vaccine of this invention, six animals of nine show an important antibody level (corresponding to neutralization indexes of 3 or more), while the neutralization indexes of the 3 other vaccinated animals are 1 or 2. These antibodies persist for the whole 27 day observation period, except for animals 77 and 82.

No local antibodies were found in the direct control animals no. 71 and 73.

Antibodies were detected before vaccination in 3 animals of which one was vaccinated. Only the vaccinated animal (No. 75) showed a significant increase of the neutralization index 11 days after vaccination.

The results in conjunction with those of Table VI demonstrate the valuable immunogenicity of the vaccine according to the invention.

g. Specificity of the local antibodies induced by vaccination.

The specificity of the local antibodies induced by vaccination was determined on concentrated pools of the nasal samplings on the 11th, 17th and 27th days after vaccination. Neutralization tests of these pools were performed against bovine Adeno 1 virus and bovine Adeno 3 virus.

TABLE IX

| Reference number of the animal | Animal status | Neutralization index of the pools after vaccination. | |
|---|---|---|---|
| | | Bovine Adeno 3 | Bovine Adeno 1 |
| 71 | direct control | 0 | 0 |
| 73 | direct control | 0 | 0 |
| 74 | vaccinated | 2 | 0 |
| 75 | vaccinated | >4 | 0 |
| 77 | vaccinated | 3 | 0 |
| 79 | vaccinated | 3 | 0 |
| 80 | vaccinated | 2 | 0 |
| 81 | vaccinated | 3 | 0 |
| 82 | vaccinated | 1 | 0 |

As appearing from Table IX, the antibodies detected in the nasal secretions are specific to bovine Adeno 3 virus. There is no cross-reaction with bovine Adeno 1 virus.

h. Symptomatology.

Starting from the vaccination date, all the animals were observed daily for temperature clinical examination for eventual ocular, respiratory and digestive symptoms.

All the observations were normal and this absence of any clinical symptom, notwithstanding the active multiplication of the vaccine strain, demonstrates the innocuity of the vaccine according to the invention.

EXAMPLE 3

The technique is that described in example 2 but the harvested supernatant fluids diluted with the said stabilizing solution are supplemented with the RLB 103 temperature-sensitive mutant strain of bovine parainfluenza 3 ($PI_3$) virus described by N. Zygraich, M. Lobmann and C. Huygelen in J. Hyg. Camb. 70, 229–34, 1972 plus the RLB 106 temperature-sensitive mutant strain of infectious bovine rhinotracheitis (IBR) virus (Research in Veterinary Science, 16,328–335(1974) and the mixture is distributed into glass vials containing $10^{6.5}$ TCID $_{50}$ of bovine Adeno 3 virus Eunice strain, $10^{7.2}$ $TCID_{50}$ of bovine $PI_3$ virus and $10^{6.8}$ $TCID_{50}$ of IBR virus or multiples of each. The vials are freeze-dried and sealed for constituting either single or multiple doses. After reconstitution by adding 4 to 5 ml. of water per dosis, the vaccine is administered as coarse spray to the animal.

Clinical trial

The trial was performed on four calves from 3 to 6 month-old (breed 'Friesian dairy cattle').

A dosage unit of the hereinabove obtained trivalent vaccine has been administered in the nostrils of each animal. Blood samples were taken for serological examination before and 6 weeks after vaccination.

The results are indicated in the following Table X.

TABLE X

| Reference number of the aminal | Serological response expressed As seroneutralizing antibodies titer for | | | | As haemagglutination inhibition titer for | |
|---|---|---|---|---|---|---|
| | Adeno 3 virus | | IBR virus | | $PI_3$ virus | |
| | before vaccination | after vaccination | before vaccination | after vaccination | before vaccination | after vaccination |
| 1 | <4 | 16 | 0 | 2 | <8 | 128 |
| 2 | <16 | 32 | 0 | 2 | 8 | 32 |
| 3 | <4 | 32 | 0 | 8 | <8 | 128 |
| 4 | 8 | 64 | 0 | 1 | 32 | 32 |

The additional bovine $PI_3$ and IBR viruses did not interfere with the Adeno 3 vaccination take and, inversely, the Adeno 3 virus did not interfere with seroconversion of the animals for the bovine $PI_3$ and IBR viruses.

We claim:

1. A polyvalent live intranasal bovine respiratory vaccine comprising (1) an intranasally effective dose of a temperature-sensitive nitrous acid mutant of a pathogenic bovine adenovirus, said mutant being protective against bovine adenovirus type 3 infection, having a cut-off temperature of from about 39° to 40°C, and being able to multiply in the upper respiratory tract of a bovine animal while having inhibited replication in the lower respiratory tract and internal organs of the body; (2) an intranasally effective dose of a vaccinal live temperature-sensitive mutant of a pathogenic infectious bovine rhinotracheitis virus; and (3) a pharmaceutical diluent.

2. A polyvalent live intranasal bovine respiratory vaccine comprising (1) an intranasally effective dose of a temperature-sensitive nitrous acid mutant of a pathogenic bovine adenovirus, said mutant being protective against bovine adenovirus type 3 infection, having a cut-off temperature of from about 39° to 40°C, and being able to multiply in the upper respiratory tract of a bovine animal while having inhibited replication in the lower respiratory tract and internal organs of the body; (2) an intranasally effective dose of a vaccinal live temperature-sensitive mutant of a pathogenic bovine parainfluenza 3 virus; and (3) a pharmaceutical diluent.

3. A polyvalent live intranasal bovine respiratory vaccine according to claim 17 comprising (1) an intranasally effective dose of a temperature-sensitive nitrous acid mutant of a pathogenic bovine adenovirus, said mutant being protective against bovine adenovirus type 3 infection, having a cut-off temperature of from about 39° to 40°C, and being able to multiply in the upper respiratory tract of a bovine animal while having inhibited replication in the lower respiratory tract and internal organs of the body; (2) an intranasally effective dose of a vaccinal live temperature-sensitive mutant of a pathogenic infectious bovine rhinotracheitis virus; (3) an intranasally effective dose of a vaccinal live temperature-sensitive mutant of a pathogenic bovine parainfluenza 3 virus; and (4) a pharmaceutical diluent.

4. A vaccine according to claim 3 in which the bovine adenovirus is type 3.

5. A vaccine according to claim 4 in which the dose of bovine adenovirus type 3 is at least $2 \times 10^6$ $TCID_{50}$.

6. A vaccine according to claim 5 in which the dose of bovine parainfluenza 3 virus is at least $10^{7.2}$ $TCID_{50}$.

7. A vaccine according to claim 6 in which the dose of infectious bovine rhinotracheitis virus is at least $10^{6.8}$ $TCID_{50}$.

8. A vaccine according to claim 1 in freeze-dried form.

* * * * *